(12) United States Patent
Cederschiöld

(10) Patent No.: US 9,089,474 B2
(45) Date of Patent: Jul. 28, 2015

(54) MEDICAL VIAL ACCESS DEVICE WITH PRESSURE EQUALIZATION AND CLOSED DRUG TRANSFER SYSTEM AND METHOD UTILIZING SAME

(71) Applicant: Becton Dickinson and Company Ltd., Dun Laoghaire, Co. Dublin (IE)

(72) Inventor: Alexander Cederschiöld, Gothenburg (SE)

(73) Assignee: Becton Dickinson and Company Ltd., Dun Laoghaire (IE)

( * ) Notice: Subject to any disclaimer, the term of this patent is extended or adjusted under 35 U.S.C. 154(b) by 0 days.

(21) Appl. No.: 13/940,809

(22) Filed: Jul. 12, 2013

(65) Prior Publication Data

US 2014/0014210 A1    Jan. 16, 2014

Related U.S. Application Data

(60) Provisional application No. 61/671,567, filed on Jul. 13, 2012.

(51) Int. Cl.
  *A61J 1/20*   (2006.01)
  *A61M 5/158*  (2006.01)
  *A61M 5/32*   (2006.01)

(52) U.S. Cl.
  CPC .............. *A61J 1/2089* (2013.01); *A61J 1/2096* (2013.01); *A61M 5/158* (2013.01); *A61M 5/1582* (2013.01); *A61M 5/3286* (2013.01); *A61J 2001/201* (2013.01); *A61J 2001/2055* (2013.01); *A61J 2001/2068* (2013.01); *A61J 2001/2072* (2013.01); *A61J 2001/2075* (2013.01); *A61J 2001/2082* (2013.01); *A61J 2200/10* (2013.01)

(58) Field of Classification Search
  CPC ......... A61J 1/14; A61J 1/2089; A61J 1/2096; A61J 2001/201; A61J 2001/2055; A61J 2001/2068; A61J 2001/2072; A61J 2001/2075; A61J 2001/2082; A61J 2200/10; A61M 2205/192; A61M 2205/195; A61M 5/158; A61M 2005/1581; A61M 5/1582; A61M 2005/1583; A61M 2005/1585; A61M 2005/1586; A61M 2005/1587; A61M 2005/1588; A61M 5/162; A61M 2005/1623; A61M 5/3286

See application file for complete search history.

(56) References Cited

U.S. PATENT DOCUMENTS 3,980,083 A * 9/1976 Elliott .......................... 604/88
4,296,786 A  10/1981 Brignola
4,834,744 A   5/1989 Ritson (Continued)

FOREIGN PATENT DOCUMENTS

FR  1600153 A     7/1970
WO  2008067511 A1 6/2008
WO  2010069359 A1 6/2010

*Primary Examiner* — Adam Marcetich
(74) *Attorney, Agent, or Firm* — The Webb Law Firm

(57) ABSTRACT

A vial access device includes a housing having first and second connectors. The first connector is configured to be secured to a first container and the second connector is configured to be secured to a second container. The vial access device further includes a spike member extending from the housing and having a proximal end and a distal end. The spike member defines a vent lumen and a fluid lumen spaced from the vent lumen with each of the vent lumen and the fluid lumen having a distal opening. A shape defined by a circumference of the spike member is only symmetric about one axis at a position between the proximal end of the spike member and the distal opening of the fluid lumen.

21 Claims, 15 Drawing Sheets

(56) References Cited

U.S. PATENT DOCUMENTS

| | | | |
|---|---|---|---|
| 4,926,915 A * | 5/1990 | Deussen et al. | 141/290 |
| 6,343,629 B1 | 2/2002 | Wessman et al. | |
| 6,409,708 B1 | 6/2002 | Wessman | |
| 6,544,246 B1 * | 4/2003 | Niedospial, Jr. | 604/411 |
| 6,715,520 B2 | 4/2004 | Andreasson et al. | |
| D637,713 S | 5/2011 | Nord et al. | |
| 8,075,550 B2 | 12/2011 | Nord et al. | |
| 2002/0128629 A1 * | 9/2002 | Antoine | 604/414 |
| 2002/0169426 A1 | 11/2002 | Takagi | |
| 2003/0229330 A1 * | 12/2003 | Hickle | 604/411 |
| 2004/0199139 A1 * | 10/2004 | Fowles et al. | 604/414 |
| 2006/0030832 A1 | 2/2006 | Niedospial et al. | |
| 2006/0178646 A1 * | 8/2006 | Harris et al. | 604/268 |
| 2006/0200095 A1 * | 9/2006 | Steube | 604/272 |
| 2007/0106244 A1 * | 5/2007 | Mosler et al. | 604/411 |
| 2007/0156112 A1 * | 7/2007 | Walsh | 604/415 |
| 2008/0172024 A1 * | 7/2008 | Yow | 604/411 |
| 2010/0147402 A1 | 6/2010 | Tornqvist | |
| 2011/0125128 A1 | 5/2011 | Nord | |
| 2012/0053555 A1 * | 3/2012 | Ariagno et al. | 604/413 |
| 2012/0179129 A1 * | 7/2012 | Imai | 604/414 |
| 2013/0085473 A1 * | 4/2013 | Weilbacher et al. | 604/513 |

* cited by examiner

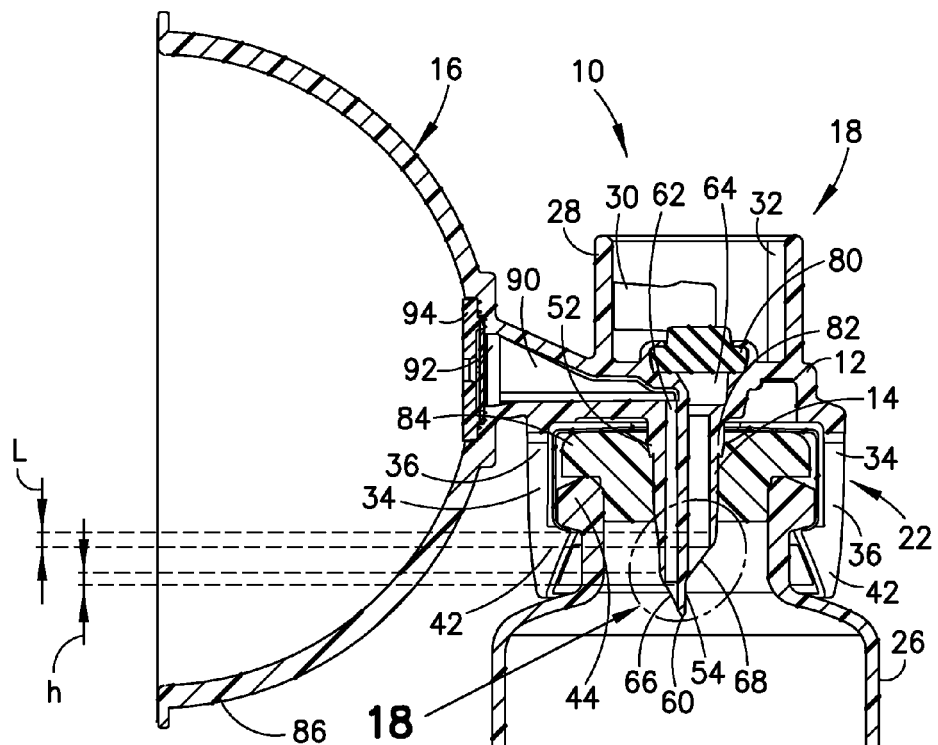
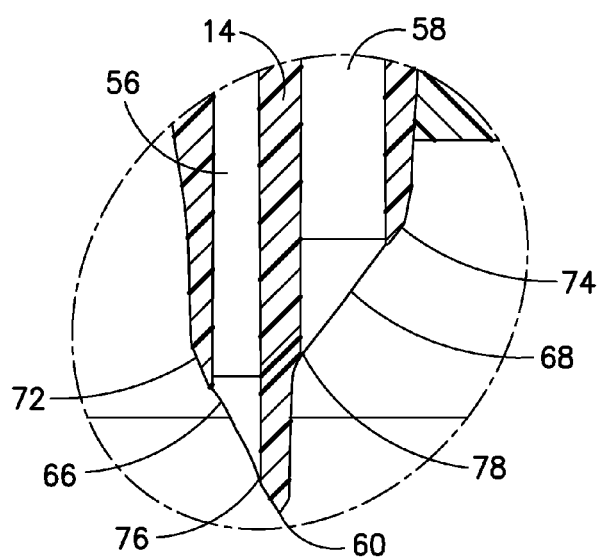
FIG. 17
FIG. 18

MEDICAL VIAL ACCESS DEVICE WITH PRESSURE EQUALIZATION AND CLOSED DRUG TRANSFER SYSTEM AND METHOD UTILIZING SAME

CROSS-REFERENCE TO RELATED APPLICATION

The present application claims priority to U.S. Provisional Application Ser. No. 61/671,567, filed Jul. 13, 2012, entitled "Medical Vial Access Device With Pressure Equalization and Closed Drug Transfer System and Method Utilizing Same", the entire disclosure of which is hereby incorporated by reference.

BACKGROUND OF THE INVENTION

1. Field of the Invention

The present invention generally relates to a connector device for connecting a first and a second fluid container. More particularly, the present invention relates to a vial connector assembly with an integral polymeric spike for penetrating a vial stopper and accessing the medicament within a vial.

2. Description of Related Art

A vial connector assembly is provided to connect a vial to a fluid container to enable the transfer of medicament between the vial and fluid connector.

For instance, a vial connector assembly is typically provided to enable the transfer of liquid medicament from a vial to a fluid container by means of an injector needle, or to enable the transfer of a dissolving solvent from a fluid container to a vial storing a dry medicament. The same vial connector assembly may also be used to attach a vial to an intravenous fitting to deliver medicament directly from the vial to a patient.

A vial connector assembly typically includes a fluid transfer device, such as a needle or spike that penetrates an elastomeric stopper or membrane sealing the opening of the vial. The fluid transfer device thus provides a means for transferring medicament from the vial to a fluid container, a means for introducing solvent into the vial, and a means for delivering medicament out of the vial.

Contemporary vial connector assemblies, however, fail to address two issues related to the transfer of medicament between a vial and a fluid container.

First, there is a potential for hazardous aerosols, particles, and vapors to leak into the environment in contemporary vial assemblies when transferring liquid medicament from a vial with an injection needle. Consequently, a user may be exposed to hazardous substances consisting of cytotoxic drugs, radio-labeled or allergy-inducing substances that may contaminate the user through inhalation or condensation on the skin of a user. Some medicaments are even known to penetrate protection gloves and thereby contaminate the user. Exposure to contaminations like this may, on a long term basis, give rise to alarmingly high concentrations of medicaments in the blood of the user.

Second, there is a potential for coring when the elastomeric stoppers of vials are pierced by a fluid transfer device, such as a sharp, metal cannulated needle, of contemporary vial connector assemblies. Coring occurs as an integral vial connector spike or an injection needle is urged through the stopper and the spike or injection needle punches or cuts a small particle of rubber from the stopper. This stopper fragment either drops into the vial or becomes lodged in the cannula and is possibly withdrawn into the syringe. In either case, the sterility of the vial contents is compromised and, in the latter case, injection of particulate matter into the patient may occur.

Contemporary devices for the aforementioned transfer of medicaments typically use a hollow pointed spike or needle for piercing an elastomeric vial stopper. Coring results from the vial connector spike or injection needle cutting a core of stopper material with the relatively sharp edges found at an intersection of an inside diameter of the spike or needle and a surface at the end of the spike or needle. These cores represent a potential health hazard if they pass along with the liquid medication into the patient's body. Also, if the cores are large enough or if there are many of them, the stopper may not retain enough material to effectively seal the vial in order to prevent leakage or to protect sterility. In addition, if the device used to puncture the stopper is too large, it may damage the stopper, even in the absence of any coring, by ripping or tearing the stopper so that it no longer effectively seals the vial.

Additionally, in many applications, the vial contents are repeatedly accessed. For instance, many injectable medicaments are packaged in multidose vials requiring vial access for the withdrawal of each unit dose. Also, many pharmaceuticals are lypholysed in sterile vials for prolonged stability. Such packaging also requires multiple vial entries to reconstitute the contents and withdrawal of the reconstituted contents. The tearing and abrasion caused by multiple vial accesses by a sharp injector needle results in pepper-like fragments contaminating the vial contents.

For the reasons stated above, there is a need for a vial connector assembly that connects a vial to a fluid container while safely enabling the transfer of medicament between the vial and fluid container while avoiding leakage or air contamination imparted by the injection needle during the transfer.

Additionally, there is a need for non-coring spike assembly that allows the transfer of medicament to and from a vial with a pierceable stopper while incurring minimal stopper damage and requiring minimal penetration forces.

SUMMARY OF THE INVENTION

In one embodiment, a vial access device includes a housing having first and second connectors. The first connector is configured to be secured to a first container and the second connector is configured to be secured to a second container. The vial access device further includes a spike member extending from the housing and having a proximal end and a distal end. The spike member defines a vent lumen and a fluid lumen spaced from the vent lumen with each of the vent lumen and the fluid lumen having a distal opening. A shape defined by a circumference of the spike member is only symmetric about one axis at a position between the proximal end of the spike member and the distal opening of the fluid lumen.

The circumference of the spike member may be oval-shaped. Further, the distal openings of the vent lumen and the fluid lumen may each be defined by a top edge and a bottom edge spaced axially from the top edge with outer portions of the top edges of the vent lumen and the fluid lumen being smooth and configured to substantially prevent coring of a stopper when penetrating the stopper with the spike member. The top edges of the vent lumen and the fluid lumen may be chamfered. The spike member may include a ring extending radially outward from the spike member with the ring being configured to engage a portion of a stopper upon penetrating the stopper with the spike member. Further, a circumference of a portion of the spike member that is positioned distally of the ring may be larger than a circumference of a portion of the spike member that is positioned adjacent to the distal openings of the vent and fluid lumens. The distal opening of the vent lumen may be axially spaced from the distal opening of the fluid lumen and the vent lumen may be positioned closer to the distal end of the spike member than the fluid lumen. The distal end of the spike member may be pointed and configured to pierce a stopper. The distal opening of the fluid lumen may extend in a longitudinal direction of the spike member. The vial access device may include a lubricant coating positioned on the spike member that is positioned adjacent to the distal end of the spike member.

The vial access device may further include a pressure equalization chamber in fluid communication with the vent lumen. A pierceable membrane may be positioned adjacent to the first connector with the pierceable membrane covering a proximal opening of the fluid lumen. The first connector may comprise a neck portion of the housing that defines an opening that is configured to receive a corresponding connector of a syringe adapter. The second connector may comprise a plurality of hook elements configured to engage a medical vial and secure the vial access device to the medical vial.

In a further embodiment, a vial access device includes a housing having first and second connectors with the first connector configured to be secured to a first container and the second connector configured to be secured to a second container. The vial access device further includes a spike member extending from the housing and having a proximal end and a distal end with the spike member defining a vent lumen and a fluid lumen spaced from the vent lumen. Each of the vent lumen and the fluid lumen have a distal opening with the distal openings of the vent lumen and the fluid lumen each defined by a top edge and a bottom edge spaced axially from the top edge. An outer portion of the top edges of the vent lumen and the fluid lumen are smooth and configured to substantially prevent coring of a stopper when penetrating the stopper with the spike member.

The top edges of the vent lumen and the fluid lumen may be chamfered. The distal opening of the vent lumen may be axially spaced from the distal opening of the fluid lumen with the vent lumen positioned closer to the distal end of the spike member than the fluid lumen. The distal end of the spike member may be pointed and configured to pierce a stopper, and the distal opening of the fluid lumen may extend in a longitudinal direction of the spike member.

In yet another embodiment, a drug transfer system includes a syringe adapter configured to be secured to a first container and a vial access device. The vial access device has a housing with first and second connectors. The first connector is configured to be secured to syringe adapter and the second connector is configured to be secured to a second container. The vial access device further includes a spike member extending from the housing and having a proximal end and a distal end with the spike member defining a vent lumen and a fluid lumen spaced from the vent lumen. Each of the vent lumen and the fluid lumen have a distal opening. A shape defined by a circumference of the spike member is only symmetric about one axis at a position between the proximal end of the spike member and the distal opening of the fluid lumen.

The spike member may include a ring extending radially outward from the spike member with the ring configured to engage a portion of a stopper upon penetrating the stopper with the spike member. A circumference of a portion of the spike member that is positioned distally of the ring may be larger than a circumference of a portion of the spike member that is positioned adjacent to the distal openings of the vent and fluid lumens.

BRIEF DESCRIPTION OF THE DRAWINGS

The various objects, advantages, and novel features of exemplary embodiments of the present invention will be more readily appreciated from the following detailed description when read in conjunction with the appended drawings, in which:

FIG. 17 is a right cross-sectional view of the vial access device shown in FIG. 1 according to one embodiment of the present invention, showing the vial access device secured to a container.

FIG. 18 is an enlarged right cross-sectional view of the vial access device shown in FIG. 1 according to one embodiment of the present invention.

Throughout the drawing figures, like reference numbers will be understood to refer to like elements, features, and structures.

DESCRIPTION OF PREFERRED EMBODIMENTS

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Figure 19:
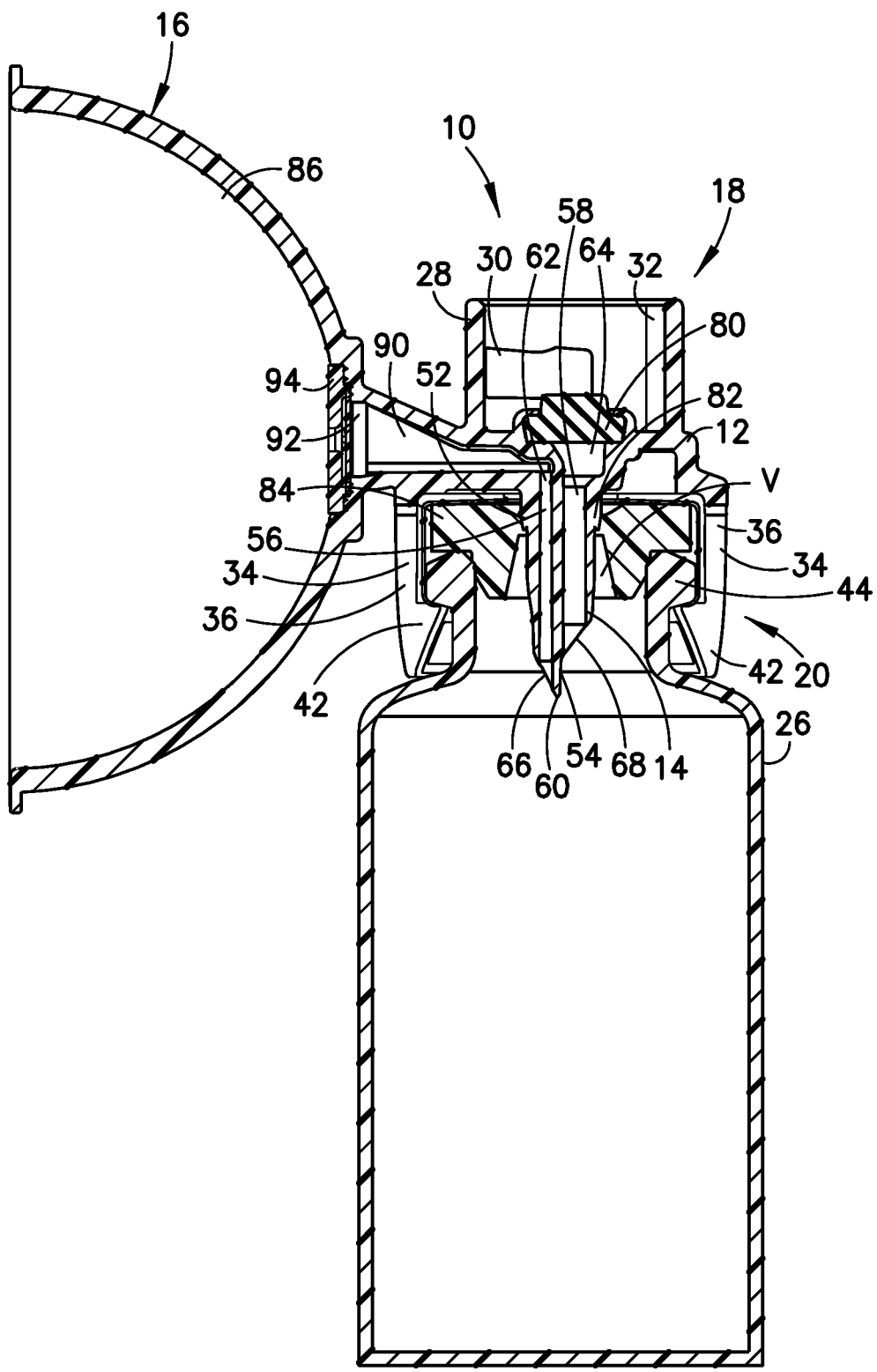
FIG. 19 is a right cross-sectional view of the vial access device shown in FIG. 1 according to one embodiment of the present invention, showing the vial access device secured to a container.
Figure 20:
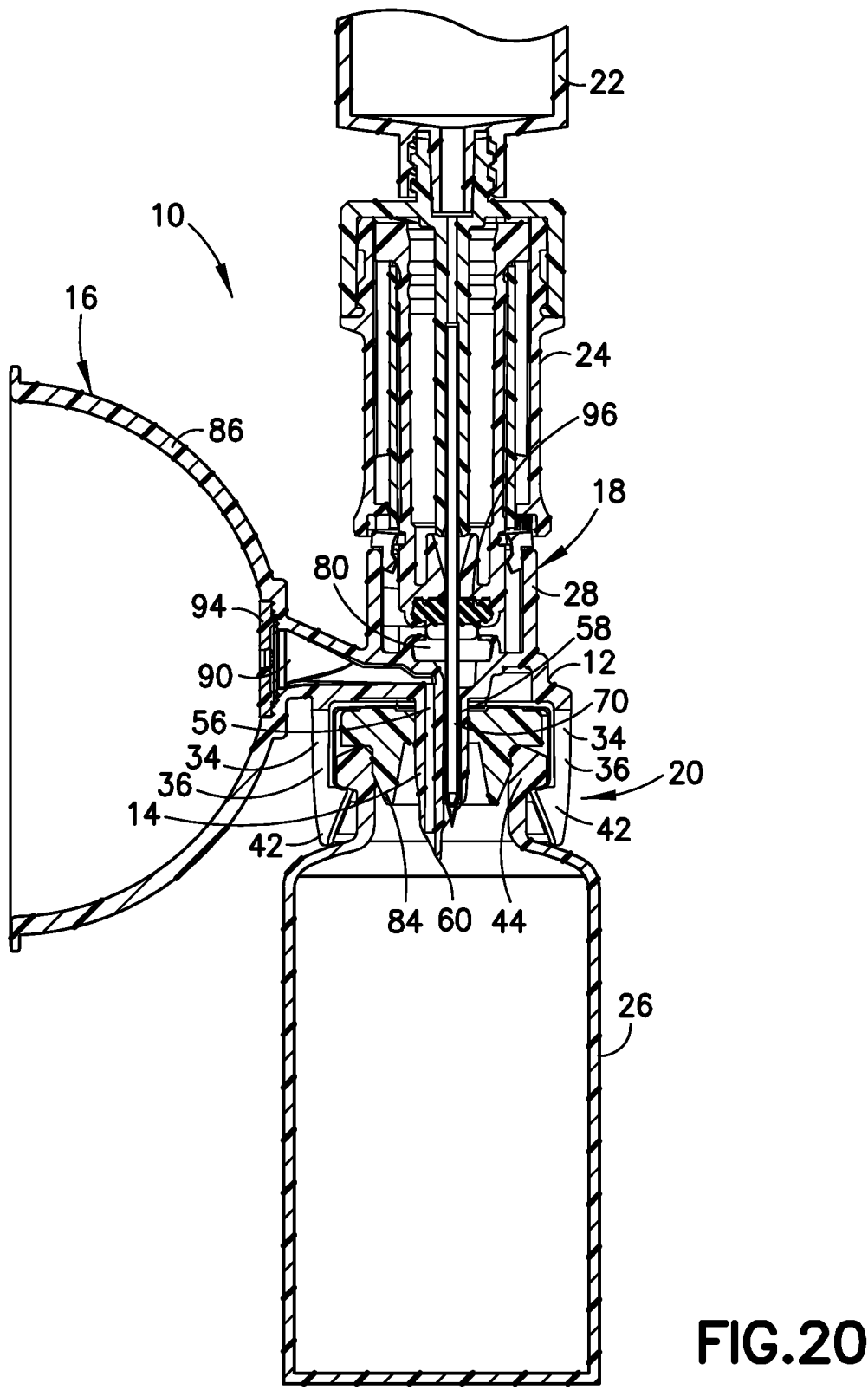
FIG. 20 is a right cross-sectional view of the vial access device shown in FIG. 1 according to one embodiment of the present invention, showing the vial access device connected to a syringe adapter and to first and second containers.

Referring to FIGS. 1-20, one embodiment of a vial access device 10 includes a housing 12, a spike member 14, and a pressure equalization chamber 16. The housing 12 includes a first connector 18 and a second connector 20 positioned opposite from the first connector 18. As shown in FIG. 20, the first connector 18 is configured to be secured to a first container 22, such as a syringe, via a syringe adapter 24. As shown in FIG. 17, the second connector 20 is configured to be secured to a second container 26, such as a medical vial. The housing 12 may be formed from a polymeric material, such as injection-molded polypropylene, although other suitable materials may be utilized. The first connector 18 is formed by a neck portion 28 of the housing 12, which defines first and second guiding grooves 30, 32 that form a bayonet-type connection with corresponding structure of the syringe adapter 24. The first and second guiding grooves 30, 32 are configured to receive and guide the corresponding structure of the syringe adapter 24. The first connector 18 is formed integrally with the housing 12, although the first connector 18 may also be formed separately. One type of connector which can be used for the first connector 18 is disclosed in U.S. Patent Application Publication No. 2011/0125128. The entire content of U.S. Patent Application Publication No. 2011/0125128 is incorporated by reference herein.

Figure 1:
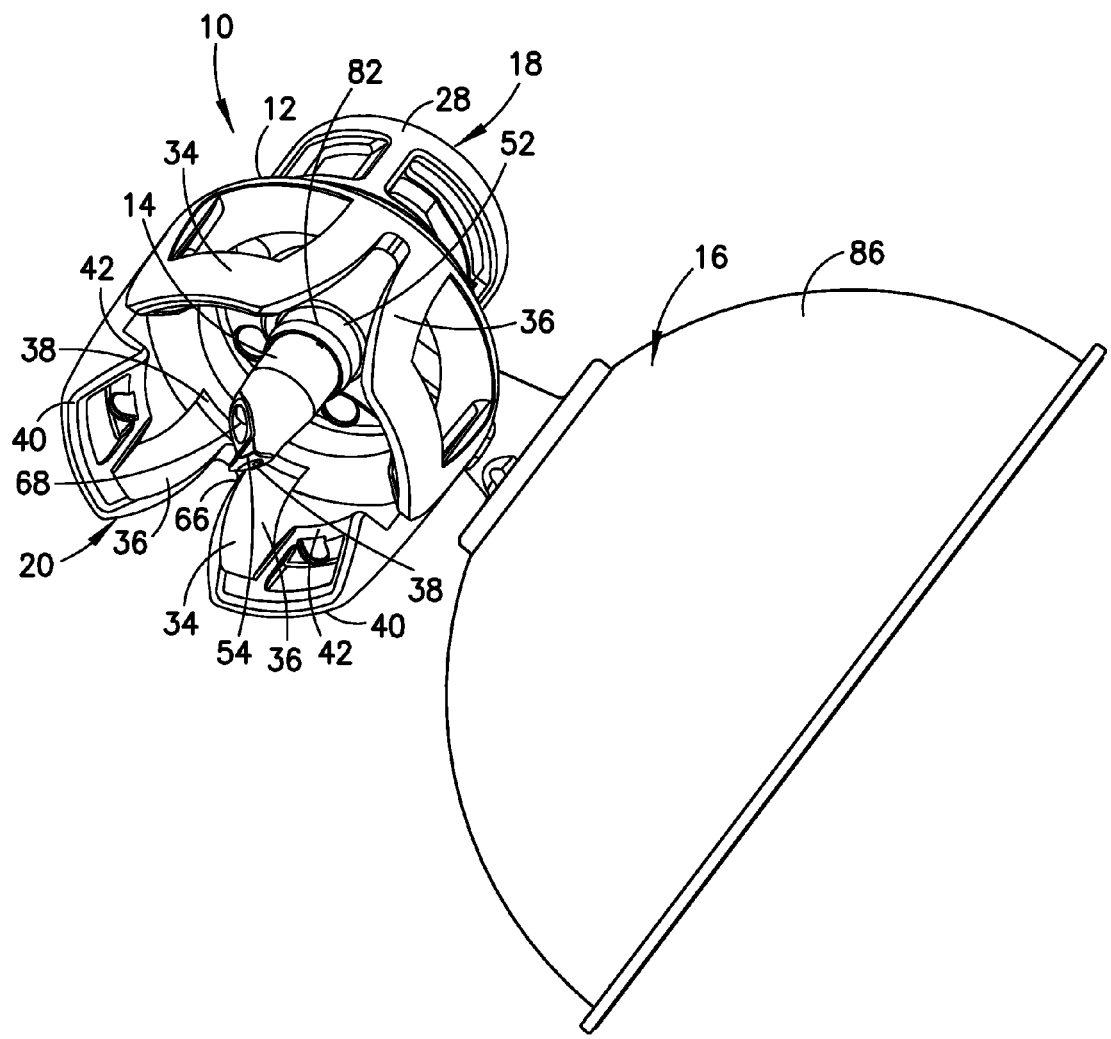
FIG. 1 is a bottom left perspective view of one embodiment of a vial access device according to one embodiment of the present invention.
Figure 2:
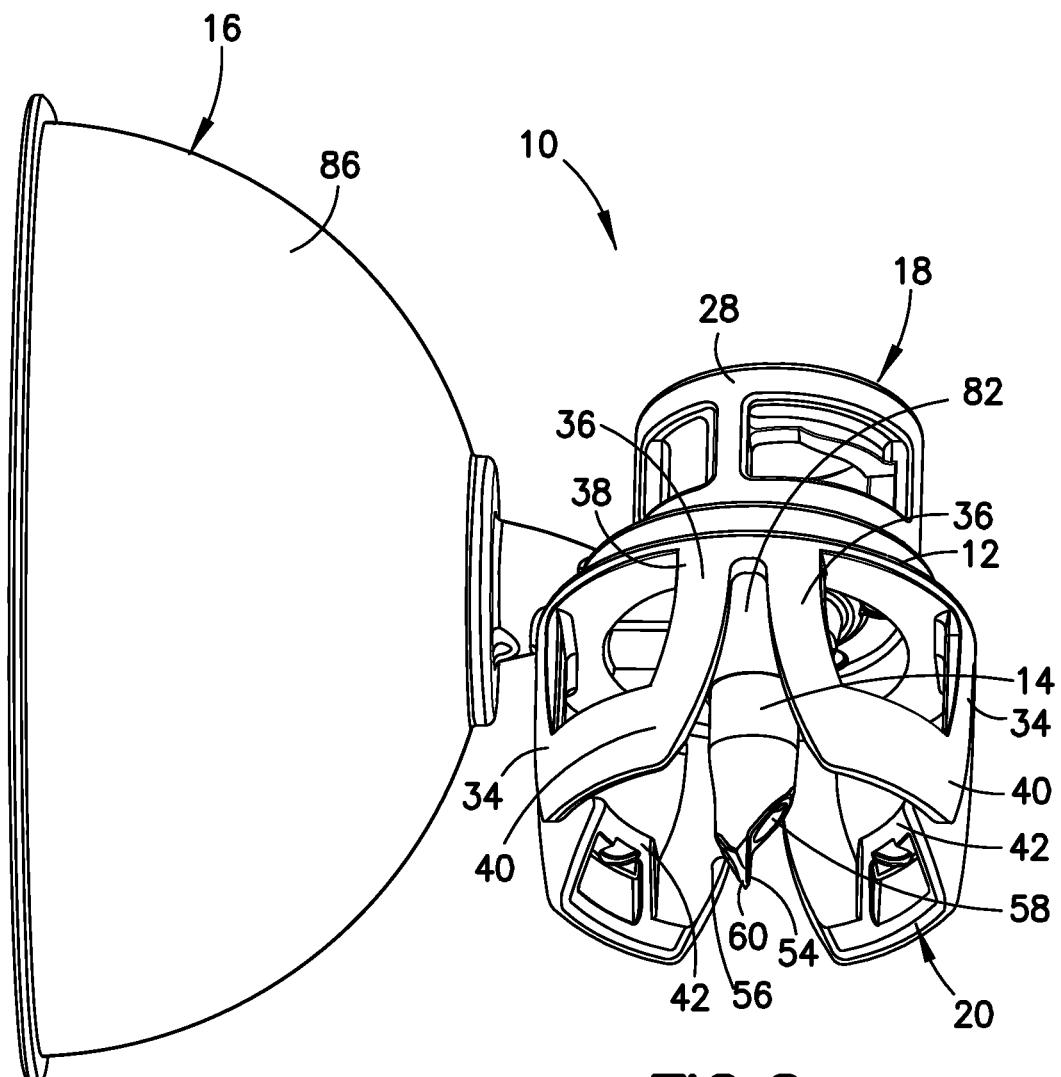
FIG. 2 is a bottom right perspective view of the vial access device shown in FIG. 1 according to one embodiment of the present invention.
Figure 3:
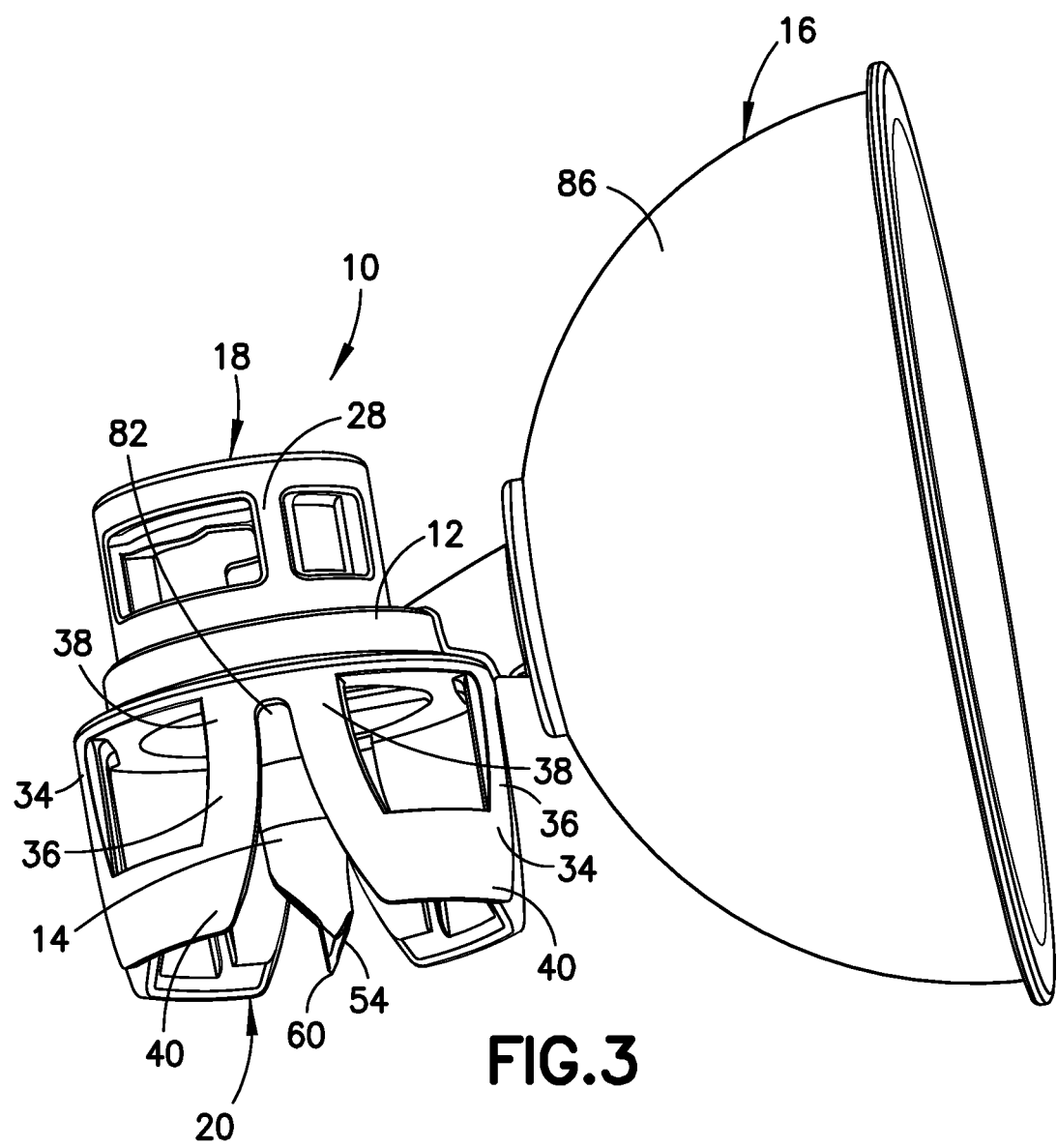
FIG. 3 is a left perspective view of the vial access device shown in FIG. 1 according to one embodiment of the present invention.
Figure 4:
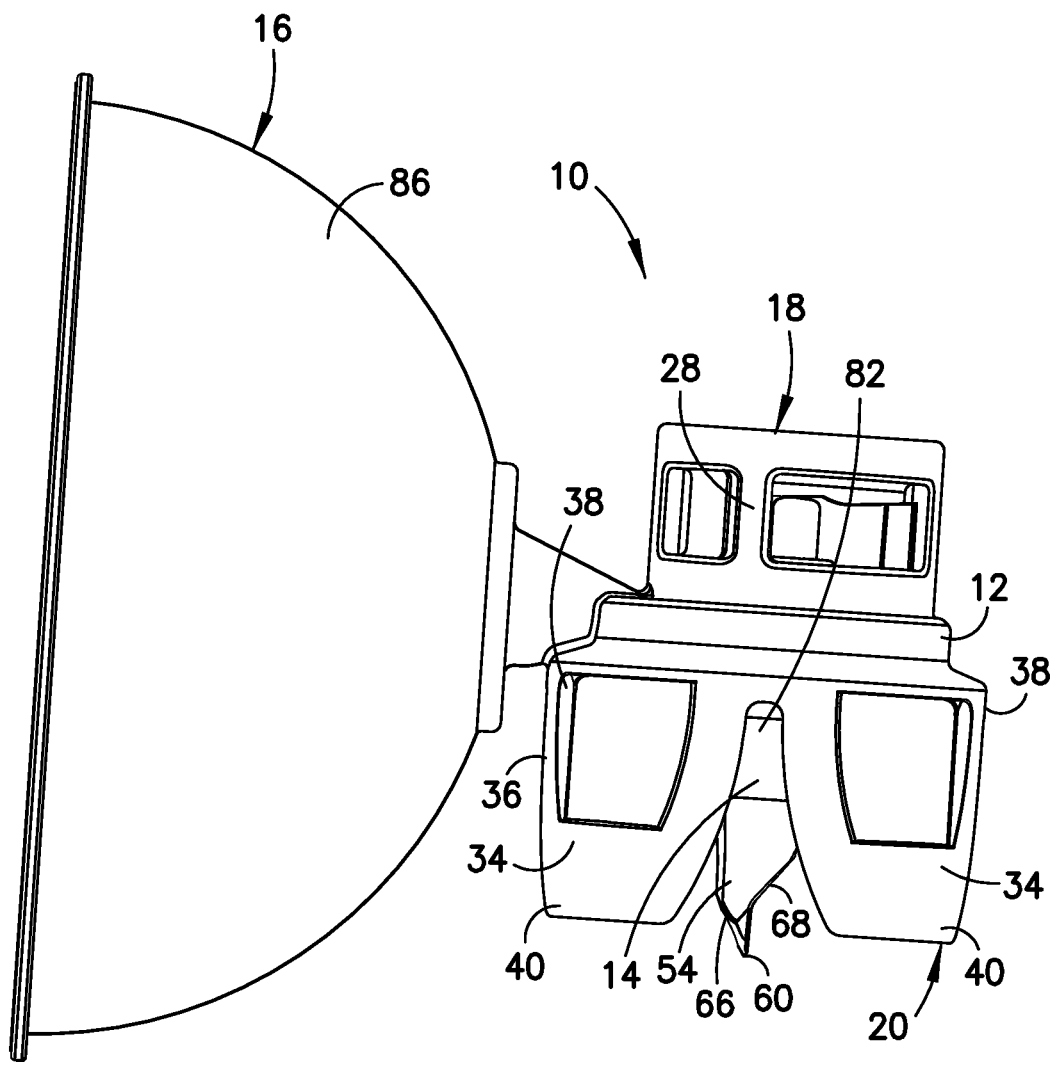
FIG. 4 is a right side view of the vial access device shown in FIG. 1 according to one embodiment of the present invention.
Figure 5:
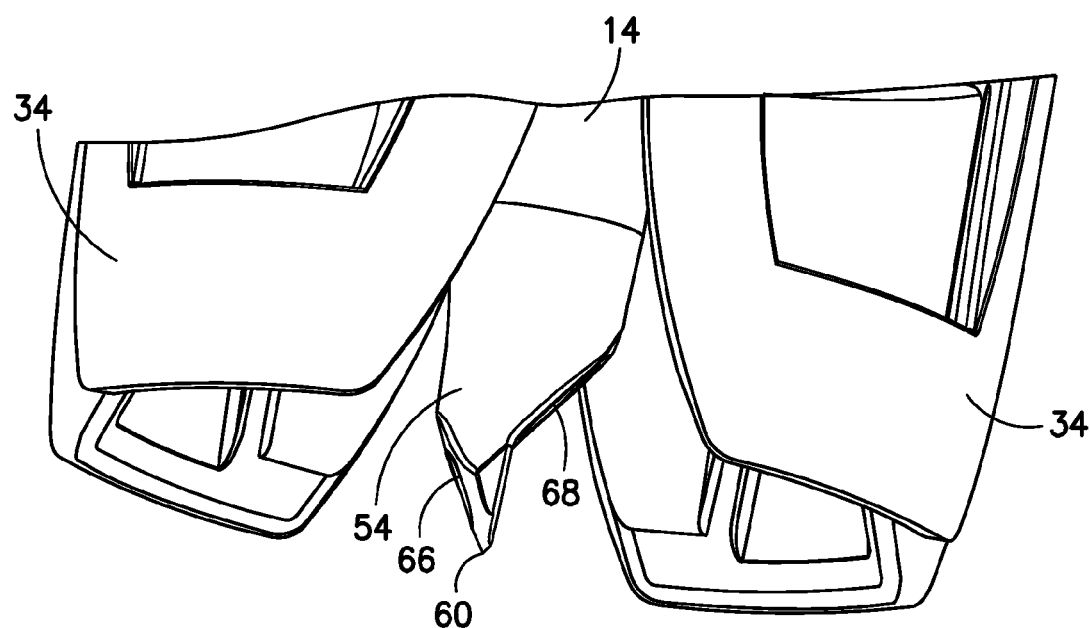
FIG. 5 is a partial right perspective view of the vial access device shown in FIG. 1 according to one embodiment of the present invention.
Figure 6:
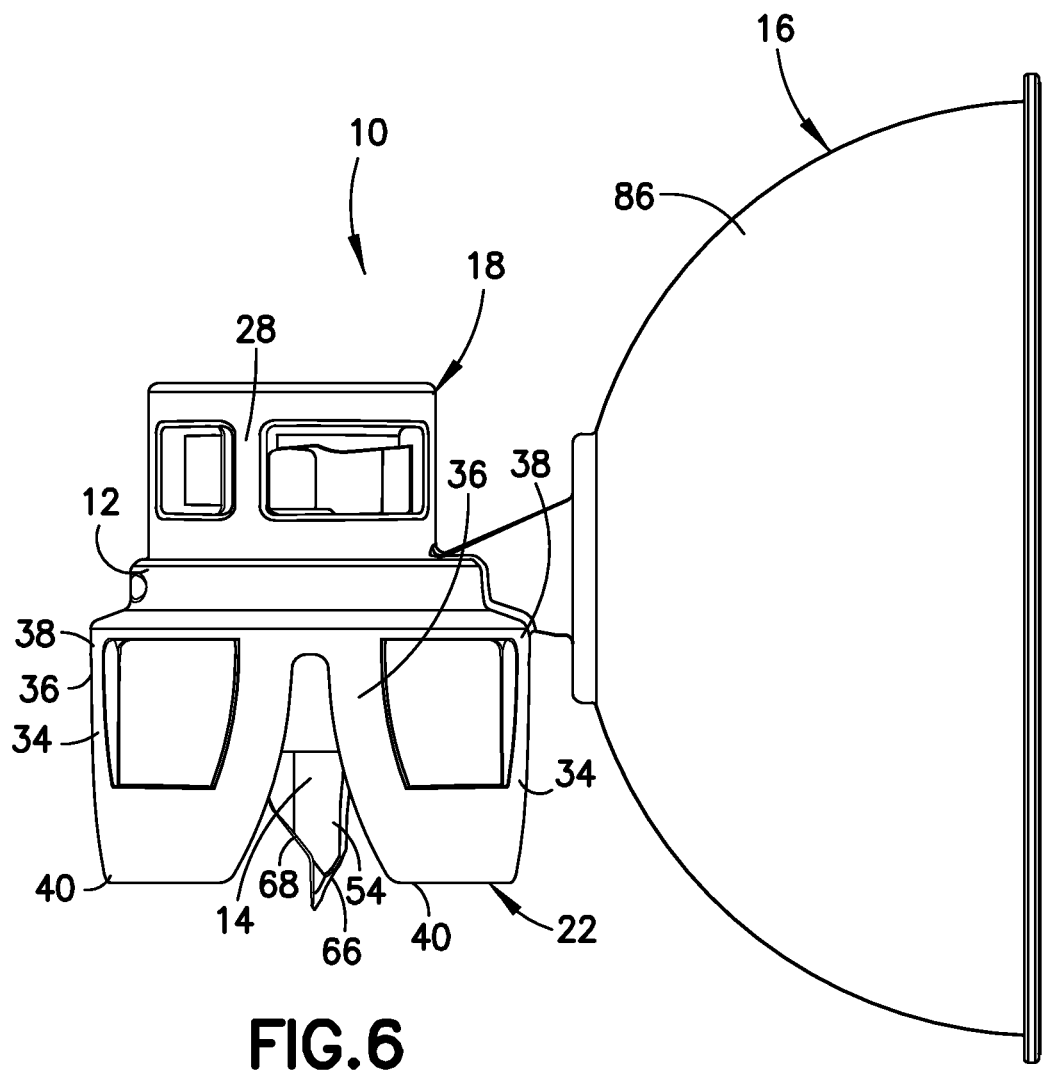
FIG. 6 is a left side view of the vial access device shown in FIG. 1 according to one embodiment of the present invention.
Figure 7:
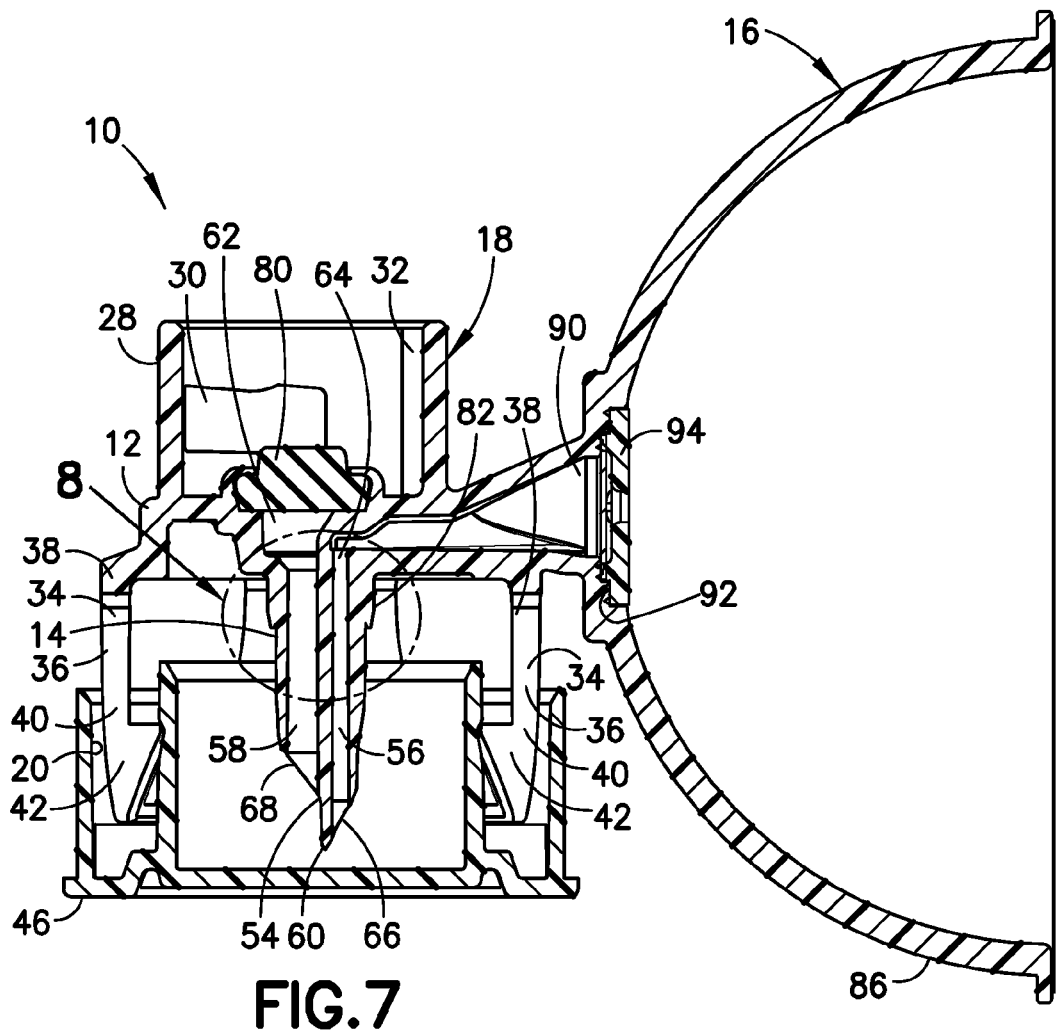
FIG. 7 is a cross-sectional, view of the vial access device shown in FIG. 1 according to one embodiment of the present invention.

The second connector 20 includes a plurality of hook elements 34 with each hook element 34 including a flexible arm 36 having proximal and distal ends 38, 40. The distal end 40 of each arm 36 has a hook protrusion 42 configured to engage a corresponding flange 44 of the second container 26, which may be a medical vial containing a medicament as shown in FIG. 17. The flexible arms 36 are configured to move radially outward upon engaging the second container 26 and subsequently return to their original position to secure the vial access device 10 to the second container 26. One type of connector which can be used for the second connector 20 is disclosed in U.S. Patent Application Publication No. 2010/0147402, which is incorporated by reference herein. As shown in FIG. 7, the second connector 20 may be covered by a protective cap 46 prior to use of the vial access device 10. In particular, the protective cap 46 is snap-fit to the exterior of the hook elements 34 to provide protection to a user from the spike member 14 and to prevent debris from entering the spike member 14 prior to use. The cap 46 may be made from a polymeric material, such as polyethylene, although other suitable materials may be utilized.

Referring still to FIGS. 1-20, the spike member 14 extends from the housing 12 and includes a proximal end 52 and a distal end 54. The spike member 12 defines a vent lumen 56 and a fluid lumen 58 spaced from the vent lumen 56. The spike member 14 extends in a direction substantially parallel to the plurality of hook elements 34 and includes a pointed tip 60 at the distal end 54 of the spike member 14. The spike member 14 is configured to pierce the second container 26 during assembly as shown in FIG. 19. The vent lumen 56 and the fluid lumen 58 each include proximal 62, 64 and distal openings 66, 68, respectively. As shown in FIG. 20, the fluid lumen 58 is configured to receive a cannula 70 from the syringe adapter 24, which extends through the housing 12 of the vial access device 10 to permit fluid to be transferred through the cannula 70 between the first and second containers 22, 26. The fluid lumen 58 extends in a longitudinal direction of the spike member 14 between the proximal opening 64 and distal opening 68 of the fluid lumen 58. The distal openings 66, 68 of the vent lumen 56 and the fluid lumen 58 are each defined by a top edge 72, 74 and a bottom edge 76, 78, spaced axially from the top edge 72, 74, respectively.

A pierceable membrane 80 is positioned adjacent to the first connector 18 and covers the proximal opening 64 of the fluid lumen 58. The pierceable membrane 80 provides a liquid and gas tight seal between the cannula 70 of the syringe adapter 24 and the pierceable membrane 80 during fluid transfer to minimize leakage and exposure of hazardous medicaments to a user. The pierceable membrane 80 may be made from a thermoplastic elastomer (TPE), although other suitable materials may be utilized. The vent lumen 56 extends longitudinally from the distal end 54 of the spike member 14 to the proximal end 52 of the spike member 14. The vent lumen 56 is aligned substantially parallel with the fluid lumen 58. The vent lumen 56 is configured to be in fluid communication with the pressure equalization chamber 16 as discussed below.

Figure 8:
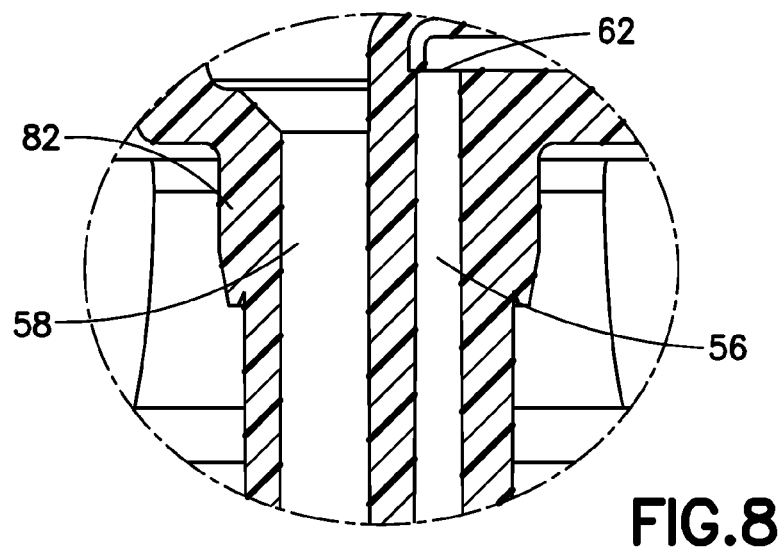
FIG. 8 is a partial cross-sectional view of the vial access device shown in FIG. 1 according to one embodiment of the present invention.
Figure 9:
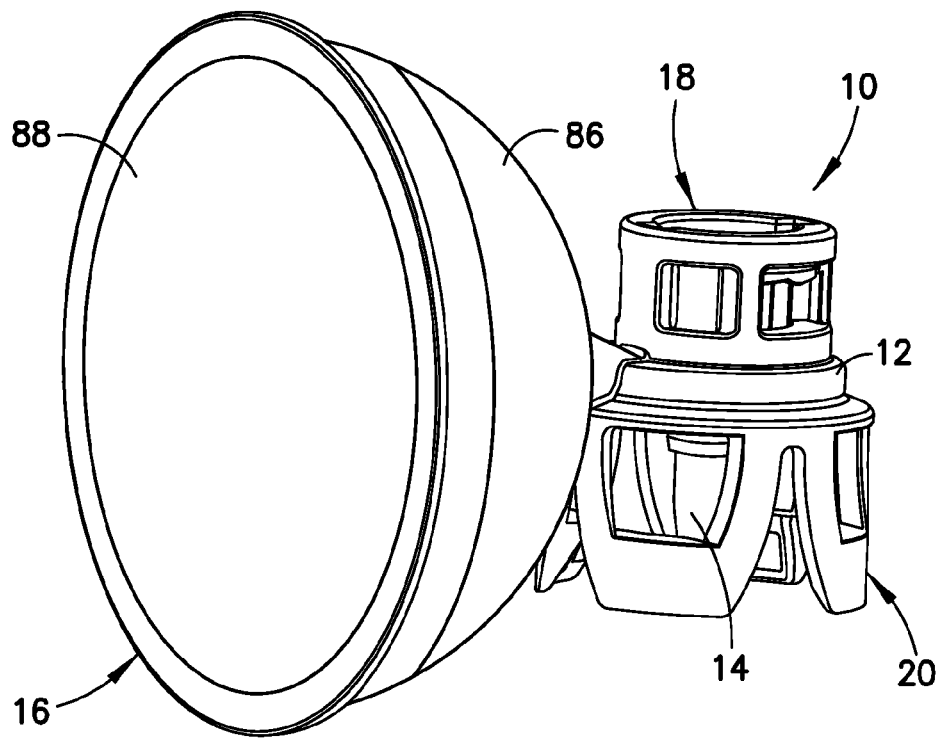
FIG. 9 is a top right perspective view of the vial access device shown in FIG. 1 according to one embodiment of the present invention, showing an expandable bladder in an unexpanded position.
Figure 10:
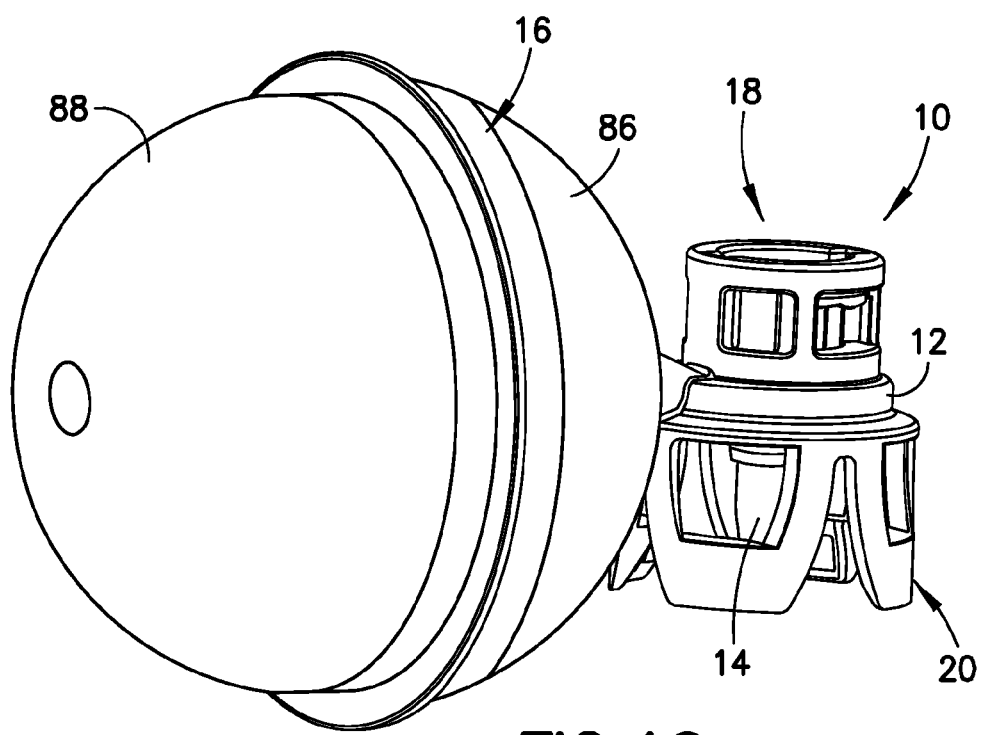
FIG. 10 is a top right perspective view of the vial access device shown in FIG. 1 according to one embodiment of the present invention, showing an expandable bladder in an expanded position.

Referring to FIGS. 7 and 8, the spike member 14 also includes a ring 82 positioned at the proximal end 52 of the spike member 14. The ring 82 extends radially outward from the spike member 14 and is configured to engage a portion of the second container 26 when the spike member 14 penetrates a seal 84 of the second container 62, such as a vial stopper of a medical vial. In one embodiment, the ring 82 may rest within the seal 84 of the second container 62 upon insertion of the spike member 14 into the second container 62. The ring 82 assists in stabilizing the vial access device 10 when the vial access device 10 is secured to the second container 26. In particular, the ring 82 may assist in preventing wobbling or a loose connection between the vial access device 10 and the second container 26. The ring 82 extends around the circumference of the spike member 14, although the ring 82 may only extend for a portion of the circumference of the spike member 14. Further, the ring 82 may be spaced from the spike member 14 to define an annular space (not shown) between the ring 82 and the spike member 14.

Referring to FIGS. 1-10, the pressure equalization chamber 16 is defined by a hemispherical or parabolic disc 86 having a thin, transparent expandable bladder 88 made of a flexible, impermeable film such as polyamide/polypropylene (PA/PP), although other suitable pressure equalization chambers and materials may be utilized. The expandable bladder 88 is moveable between an unexpanded state (shown in FIG. 9) and an expanded state (shown in FIG. 10), which acts to maintain a predetermined pressure within the second container 26. The transition of the expandable bladder 88 between the unexpanded state and the expanded state occurs during fluid transfer, which is described in more detail below.

The pressure equalization chamber 16 is in fluid communication with the vent lumen 56 via a pressure chamber channel 90, which extends about perpendicular to the vent lumen 56. The pressure chamber channel 90 has an opening 92 that is positioned substantially at the center of the disc 86. A barrier filter 94 is positioned at the opening 92 of the pressure chamber channel 90 between the pressure equalization chamber 16 and the pressure chamber channel 90. In particular, the barrier filter 94 covers the opening 92 of the pressure chamber channel 90 and prevents fluid from reaching the expandable bladder 88 and the volume defined by the disc 86 and the expandable bladder 88. The barrier filter 94 is preferably a hydrophobic filter which permits gas to pass but prevents liquid from passing through. The barrier filter 94 may be made of polytetrafluoroethylene (PTFE or Teflon®) with a pore size of between 0.1-5 μm and preferably about 3 μm. Upon connecting the vial access device 10 to the second container 26, the pressure equalization chamber 16 will be in fluid communication with the second container 26 via the pressure chamber channel 90 and the vent lumen 56.

Referring to FIGS. 17-20, the operation of the vial access device 10, according to one embodiment of the present invention, will be described in greater detail. The vial access device 10 is assembled via the first connector 18 to the syringe adapter 24, which is connected to the first container 22, such as a syringe. Further, the vial access device 10 is secured to the second container 26 via the second connector 20. After assembly, a user is able to introduce fluid into the second container 26 and retract fluid from the second container 26. One example of a syringe adapter 24 is disclosed in U.S. Pat. No. 8,075,550. The entire content of U.S. Pat. No. 8,075,550 is incorporated by reference herein. During use, the vial access device 10 is initially secured to the second container 26 via the second connector 20 as shown in FIG. 17. The hook elements 34 fixedly connect the vial access device 10 to the second container 26 as the flexible arms 36 having the hook protrusions 42 engage the corresponding flange 44 on the second container 26. As the vial access device 10 is secured to the second container 26, the distal end 54 of the spike member 14, particularly the pointed tip 60, pierces the stopper or septum 84 that covers and seals the opening of the second container 26. The syringe adapter 24 and the first container 22 are then secured to the vial access device 10 via the first connector 18. As shown in FIG. 20, the corresponding connector of the syringe adapter 24 is received by the first connector 18 of the vial access device 10 and releasably secures the syringe adapter 24 to the vial access device 10. The membrane 80 of the vial access device 10 engages a membrane 96 of the syringe adapter 24 when the syringe adapter 24 is secured to the vial access device 10 to form a leak-free connection between the syringe adapter 24 and the vial access device 10.

Referring to FIG. 20, to introduce fluid into the second container 26, the cannula 70 of the syringe adapter 24 pierces the membrane 96 of the syringe adapter 24 and the membrane 80 of the vial access device 10 and extends through the fluid lumen 58 of the spike member 14. A diluent may be introduced from the first container 22 through the syringe adapter 24 and into the second container 26 via the vial access device 10 to reconstitute a lyophilized medicament contained within the second container 26. As fluid is introduced through the cannula 70 of the syringe adapter 24, air within the second container 26 is displaced through the vent lumen 56 and the pressure chamber channel 90 and into the pressure equalization chamber 16, thereby causing the expandable bladder 88 to expand from the unexpanded state shown in FIG. 9 to the expanded state shown in FIG. 10. The vial access device 10, first and second containers 22a, 26, and the syringe adapter 24 may then be inverted from the position shown in FIG. 20 to reconstitute the medicament within the second container 26 and subsequently withdraw the reconstituted medicament into the first container 22 using any suitable arrangement, such as through the use of a syringe plunger. During transfer of fluid from the second container 26 to the first container 22, the previously displaced air within the pressure equalization chamber 16 will flow through the pressure chamber channel 90 and the vent lumen 56 into the second container 26, which prevents a vacuum from being drawn on the second container 26. At that point, the bladder 88 of the pressure equalization chamber 16 will have moved from the expanded state to the unexpanded state. The cannula 70 of the syringe adapter 24 is then withdrawn from the second container 26 and the vial access device 10. The syringe adapter 24 can then be removed from the vial access device 10 with the first container 22 having the medicament ready for transport or delivery to a patient via a suitable arrangement, such as through an infusion set.

Because the cannula 70 of the syringe adapter 24 extends through the fluid lumen 58 of the spike member 14, the cannula 70 does not have to pierce or penetrate the stopper or septum 84 of the second container 26 with each access to the second container 26. Accordingly, the tearing, abrasion, and cutting caused by multiple penetrations of the stopper 84 by the cannula 70 of the syringe adapter 24 can be eliminated, thereby reducing the possibility of contaminating the contents of the second container 26 from fragments torn from the stopper 84. The spike member 14 of the vial access device 10 allows the contents of the second container 26 to be emptied with only one penetration of the stopper 84, which reduces the chance of coring of the stopper 84.

The stopper or septum 84 of the second container 26 have various designs but generally are all press-fitted into the second container 26 to form a radial seal. Certain stopper designs utilize a solid thick body with a coated bottom surface. The rubber material used for the stopper may be substantially incompressible such that the portion of a device that penetrates the stopper needs to displace the same volume of the stopper in the container. In conventional devices, such displacement may lead to coring of the stopper, which can lead to the removed portion of the stopper blocking the air passage through a vial adapter or falling into the vial and contaminating its contents.

Referring again to FIGS. 1-20, the spike member 14, according to one embodiment of the present invention, has a variable cross-section along its longitudinal length to minimize the volume of the penetrating part of the spike member 14. More specifically, a shape defined by a circumference of the spike member 14 is only symmetric about one axis at a position between the proximal end 52 of the spike member 14 and the distal opening 68 of the fluid lumen 58. The minimized volume of the oval-shaped spike member 14 serves to minimize the volume of the stopper 84 of the second container 26 that needs to be compressed or displaced, thereby reducing coring of the stopper 84.

Referring to FIGS. 12-16, the shape of the circumference and cross-section of the spike member 14 is oval-shaped. The cannula 70 of the syringe adapter 24 has an inner diameter D1 and an outer diameter D2. The fluid lumen 58 has an inner diameter of D3, which is preferably equivalent to D2+(D2−D1). The vent lumen 56 has an inner diameter of D4, which is preferably smaller or equivalent to the inner diameter D1 of the cannula 70 of the syringe adapter 24. The flow rate from the cannula 70 is maintained due to the smaller or equivalent size of the inner diameter D1 of the cannula 70 and the diameter D4 of the vent lumen 56. In one embodiment, the width of the oval-shaped spike member 14 along the Y-axis is equivalent to D3+3T1+D4 at line 15-15 shown in FIG. 12. The width of the spike member 14 along the X-axis is equivalent to D3+2T1 at line 15-15 shown in FIG. 12. The circumference of the spike member 14 is continuous without any external splines, ribs, or notches, which seals against the stopper 84 of the second container 26 during penetration, thereby preventing leakage that may otherwise occur if the exterior surface was uneven.

In conventional devices, needles with circular-shaped cross-sections typically provide adequate leakage protection by sealing against the stopper of a container, such as a medical vial, when accessing the vial. A circular-shaped spike, however, would generate too large of a volume and lead to coring issues due to the displacement of the stopper of the second container by the circular-shaped spike. The oval-shaped circumference and cross-section of the spike member 14, according to one embodiment of the present invention, provides leakage protection while minimizing the volume of the spike member 14.

Figure 12:
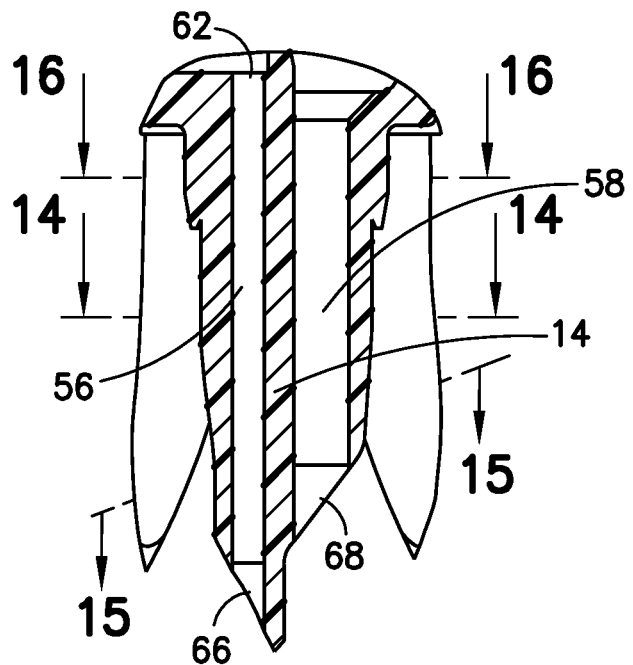
FIG. 12 is a partial front cross-sectional view of the vial access device shown in FIG. 1 according to one embodiment of the present invention.
Figure 13:
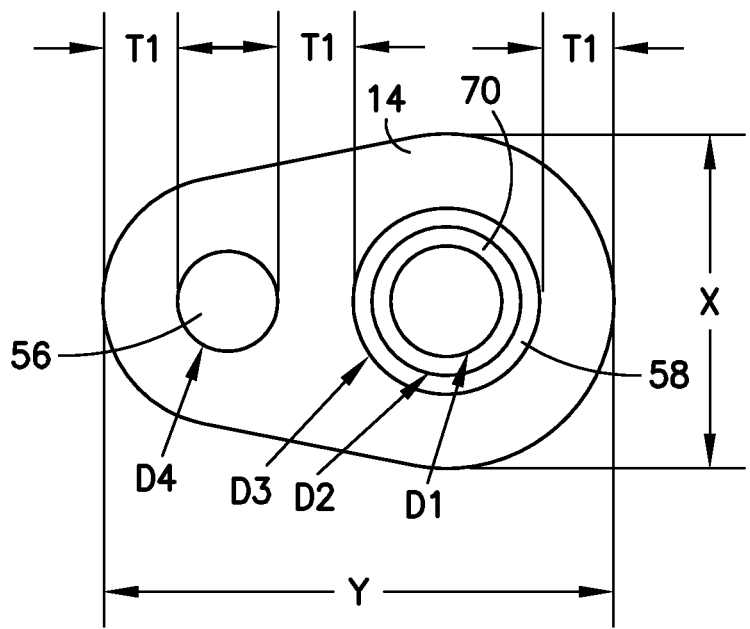
FIG. 13 is a partial bottom cross-sectional view of the vial access device taken along line 15-15, showing a cannula of a syringe adapter received within a fluid lumen of the vial access device.
Figure 14:
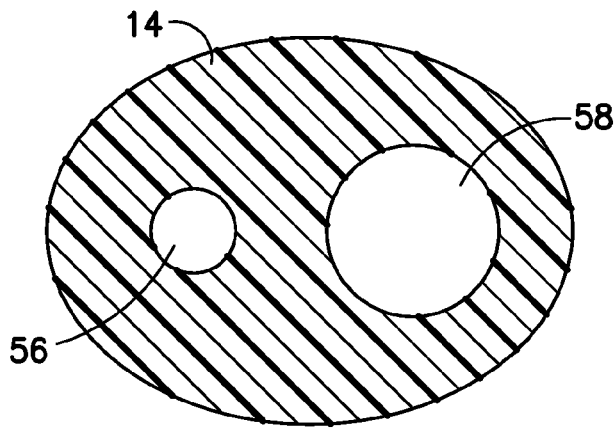
FIG. 14 is a partial bottom cross-sectional view of the vial access device taken along line 14-14 shown in FIG. 12.
Figure 15:
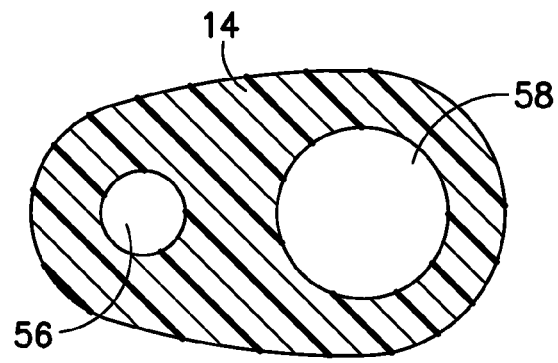
FIG. 15 is a partial bottom cross-sectional view of the vial access device taken along line 15-15 shown in FIG. 12.
Figure 16:
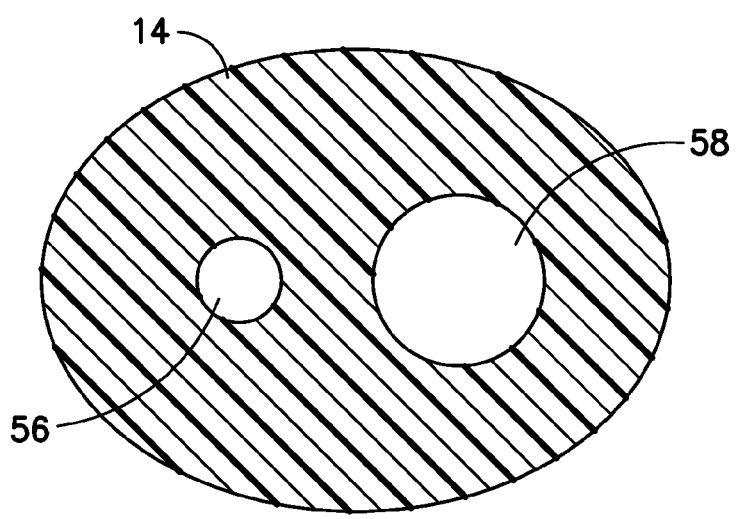
FIG. 16 is a partial bottom cross-sectional view of the vial access device taken along line 16-16 shown in FIG. 12.

Referring to FIGS. 14-17, the proximal end 52 of the spike member 14 is more symmetrical and larger then the distal end 54 of the spike member 52. In particular, the shape defined by the circumference of the spike member 14 adjacent to the distal end 54 of the spike member 14 is only symmetrical along one axis as shown in FIG. 15. The proximal end 52 of the spike member 14 is more symmetrical and larger in order to seal the spike member 14 against the stopper 84 of the second container 26 to prevent leakage when the vial access device 10 rotates on the second container 26, which can occur when the syringe adapter 24 is connected to the vial access device 10 or when the first container 22 is rotated. The distal end 54 of the spike member 14 is smaller compared to proximal portions of the spike member 14 in order to minimize the volume of the spike member 14 and prevent major displacement of the stopper 84 of the second container 26 when penetrated by the spike member 14. The spike member 14 is thinner at the distal end 54, but still has the required rigidity to penetrate the stopper 84 of the second container 26. As shown in FIG. 12, the portion of the spike member 14 positioned distally from the ring 82 tapers in size from the size of the spike member 14 shown in FIG. 14 to the size of the spike member 14 shown in FIG. 15. As discussed above, the ring 82 extends radially outward from the spike member 14 and has a larger circumference than portions of the spike member 14 positioned distally from the ring 82. Thus, the circumference of the portion of the spike member 14 that is positioned distally of the ring 82 is larger than a circumference of a portion of the spike member 14 that is positioned adjacent to the distal openings 66, 68 of the vent and fluid lumens 56, 58. As shown in FIG. 17, the ring 82 only penetrates a portion of the stopper 84 of the second container 26 and acts to stabilize the vial access device 10 when secured to the second container 26.

Furthermore, in conventional devices, the top edge of the channel openings of a needle or cannula can cut into the stopper of a fluid container. The spike member 14 according to one embodiment of the present invention overcomes this problem by rounding the top edge 72, 74 of the distal openings 66, 68 of the vent lumen 56 and the fluid lumen 58. The rounding or blunting of the top edge 72, 74 (i.e., the heel) of the distal openings 66, 68 of the vent and fluid lumens 56, 58 provides outer portions of the top edges 72, 74 of the vent lumen 56 and the fluid lumen 58 that are smooth to substantially prevent coring of the stopper 84 of the second container 26, such as a medical vial, when penetrating the stopper 84 with the spike member 14. The top edge 72, 74 of the distal openings 66, 68 of the vent lumen 56 and the fluid lumen 58 is chamfered, although other processes may be utilized to provide smooth top edges 72, 74 to prevent coring, such as providing a radius.

Referring to FIG. 18, the distal openings 66, 68 of the vent lumen 56 and the fluid lumen 58 are formed by cut-outs C1, C2 and allows for the top edges 72, 74 of the vent lumen 56 and the fluid lumen 58 to be smooth. The distal openings 66, 68 of the vent lumen 56 and fluid lumen 58 are provided at an angle and extend in the longitudinal direction of the spike member 14. A radius R of the edges of the cut-outs C1, C2 may be at least 0.05-0.1 mm or larger. In certain embodiments, the length of the fluid lumen 58 and the vent lumen 56 are optimized to fit the thickest stopper or septum 84 used for the second container 26 in order to be utilized with the majority of commercially available stoppers.

Referring to FIG. 17, the placement of the distal openings 66, 68 of the vent lumen 56 and fluid lumen 58 in relation to the hook elements 34 along the longitudinal axis of the spike member 14 determines the distal openings 66, 68 placement in relation to the bottom of the stopper 84. The distance L, which may be approximately 0.64 mm in an exemplary embodiment, separates the planar surface of the hook protrusion 42 of the hook element 34 and the proximal opening 64 of the fluid lumen 58 along the longitudinal axis of the spike member 14. Distance h, which may be approximately 1.67 mm in an exemplary embodiment, separates the distal opening 68 of the fluid lumen 58 and the proximal opening 62 of the vent lumen 56 along the longitudinal axis of the spike member 14.

Referring to FIGS. 17 and 19, the relatively large volume of the spike member 14 is advantageous because the spike member 14 fills a dead volume V between the stopper 84 and the spike member 14 that would be created by a thinner spike, which is illustrated in FIG. 19.

Figure 11:
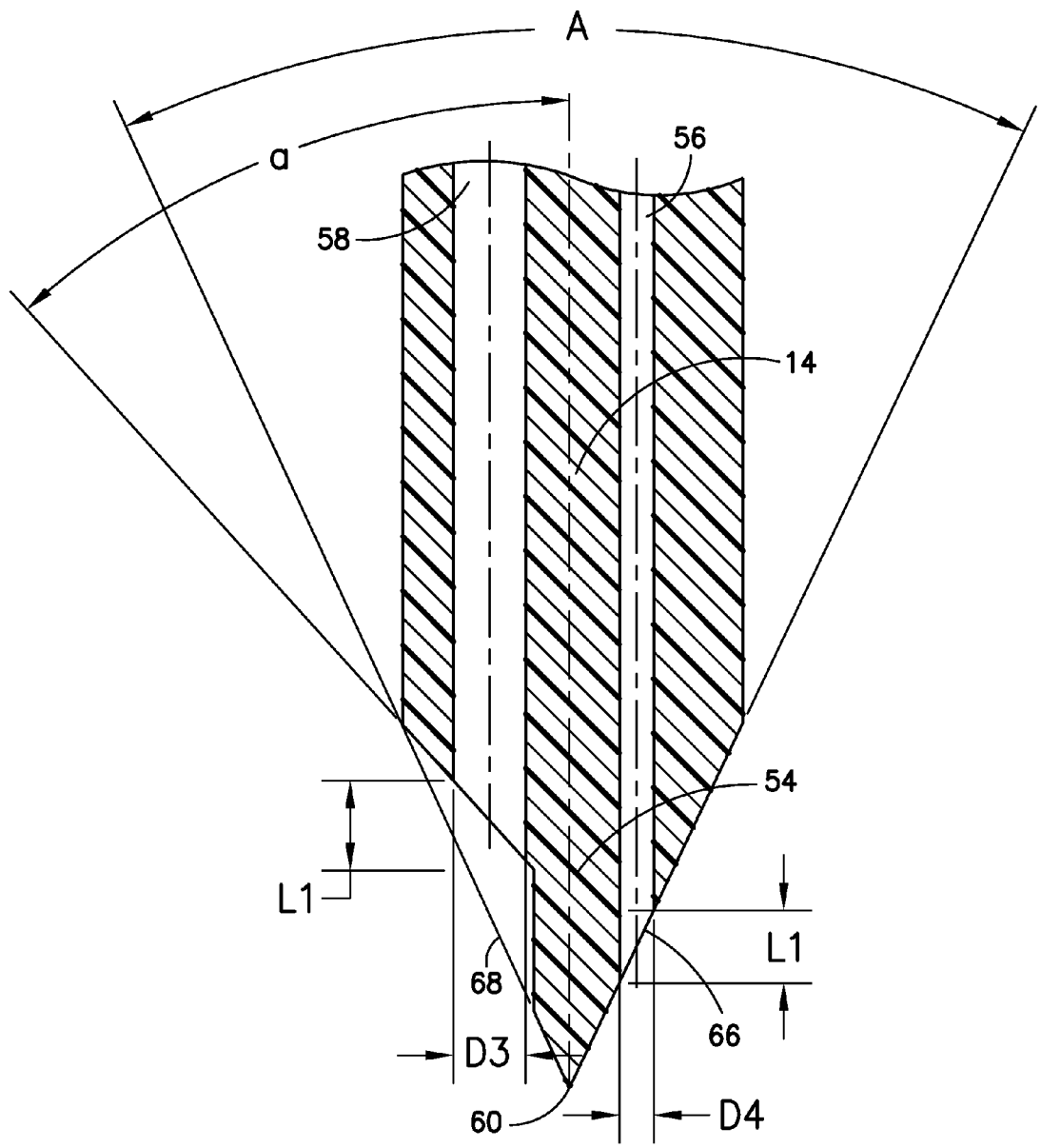
FIG. 11 is a partial schematic cross-sectional view of the vial access device shown in FIG. 1 according to one embodiment of the present invention.

Referring to FIG. 11, the relationship between an angle A of the distal end 54 of the spike member 14 and the length L1 of the distal openings 66, 68 of the vent lumen 56 and the fluid lumen 58 along the longitudinal axis can be defined by: L1=D6/tan(A/2)=D5/tan(a/2), where D6 is the diameter of the vent lumen 56, D5 is the diameter of the fluid lumen 58, and angle a is a cut-out angle of the fluid lumen 58. In one embodiment, the angle A and cut-out angle are smaller sized or optimized for easier penetration of the stopper 84 of the second container 26. In one embodiment, the length L1 of the distal openings 66, 68 of the spike member 14 are shorter in the longitudinal direction of the spike member 14 than the thickness of the thinnest stopper according to ISO 8362-2: 2008 in order to prevent leakage during penetration of the stopper 84. If the distal openings 66, 68 are longer than the thickness of the stopper 84, there will be an open channel for a short time during penetration and leakage may occur through the open channel due to the pressurized contents of the second container 26.

Referring to FIG. 17, in an exemplary embodiment, the distal opening 66 of the vent lumen 56 is positioned as close to the distal end 54 of the spike member 14 (i.e., near the pointed tip 60) as possible and as far away from the distal opening 68 of the fluid lumen 58 as possible to minimize the risk of air entering the fluid lumen 58 when extracting liquid from the second container 26.

Figure 21:
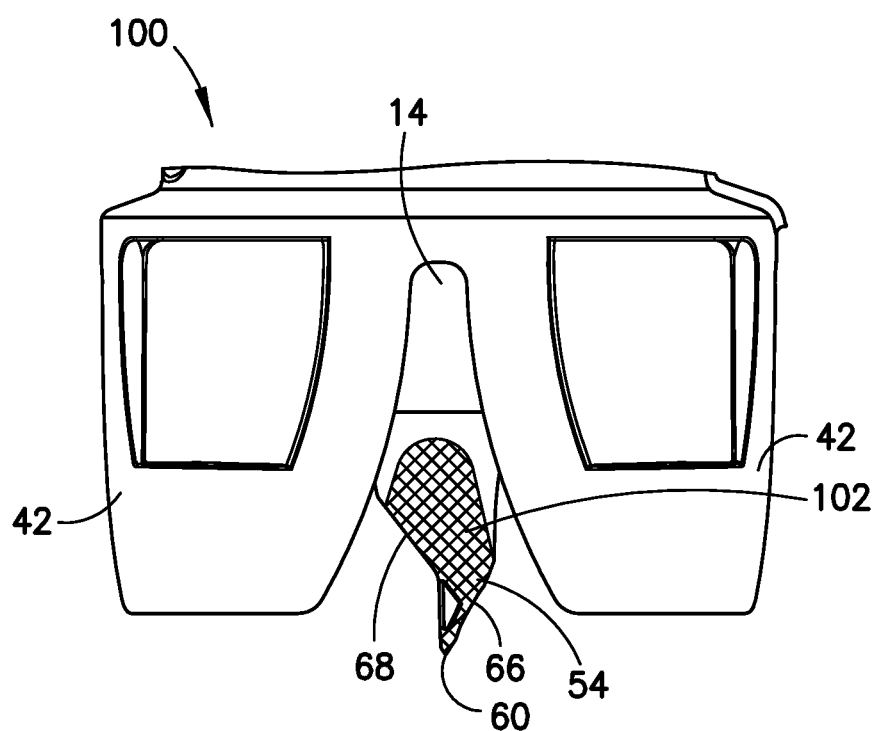
FIG. 21 is a partial left side view of a vial access device according to a second embodiment of the present invention.

Referring to FIG. 21, a further embodiment of a vial access device 100 is shown. The vial access device 100 shown in FIG. 21 is the same as the vial access device 10 described above and shown in FIGS. 1-20 except that the vial access device 100 of the present embodiment includes a lubricant coating 102 applied to an exterior surface of the spike member 14. The lubricant coating 102 reduces the friction caused by the penetration of the spike member 14 into the stopper 84 of the second container 26. The lubricant coating 102 may be silicone-based, although other suitable lubricant coatings may be utilized. In an exemplary embodiment, the lubricant coating 102, which is shown by cross-hatching in FIG. 21, is applied close to the pointed tip 60 of the spike member 14 and over the distal openings 66, 68 of the fluid lumen 58 and the vent lumen 56. The lubricant coating 102 can be applied by a modified transfer pad (tampon) printing process and migrates over time to cover approximately 70% of the surface of the spike member 14, although other suitable processes for applying the coating 102 may be utilized.

The individual components used in the exemplary vial access devices 10, 100 disclosed herein can be based on existing designs and components which are known in the art. The following additional U.S. patent documents, which are incorporated by reference herein, disclose exemplary components and subsystems which may be used in the practice of the present invention: U.S. Pat. Nos. 6,343,629; 6,409,708; 6,715,520; 8,075,550; 2010/0147402; 2011/0125128; and D637,713.

While certain exemplary embodiments of the present invention have been shown and described herein with reference to certain preferred embodiments thereof, it will be understood by those skilled in the art that various changes in form and details may be made therein without departing from the spirit and scope of the invention.

What is claimed is:

1. A vial access device comprising:
   a housing having first and second connectors, the first connector configured to be secured to a first container, the second connector configured to be secured to a second container;
   a spike member extending from the housing and having a proximal end and a distal end, the spike member defining a vent lumen and a fluid lumen spaced from the vent lumen, each of the vent lumen and the fluid lumen having a distal opening, wherein a shape defined by a circumference of the spike member is only symmetric about one axis at a position between the proximal end of the spike member and the distal opening of the fluid lumen, wherein the circumference of the spike member varies in size and shape between the proximal end of the spike member and the distal opening of the fluid lumen.

2. The vial access device of claim 1, wherein the circumference of the spike member is substantially oval-shaped.

3. The vial access device of claim 1, wherein the distal openings of the vent lumen and the fluid lumen are each defined by a top edge and a bottom edge spaced axially from the top edge, outer portions of the top edges of the vent lumen and the fluid lumen are smooth and configured to substantially prevent coring of a stopper when penetrating the stopper with the spike member.

4. The vial access device of claim 3, wherein the top edges of the vent lumen and the fluid lumen are chamfered.

5. The vial access device of claim 1, wherein the spike member comprises a ring extending radially outward from the spike member, wherein the ring is configured to engage a portion of a stopper upon penetrating the stopper with the spike member, and wherein a circumference of a portion of the spike member that is positioned distally of the ring is larger than a circumference of a portion of the spike member that is positioned adjacent to the distal openings of the vent and fluid lumens.

6. The vial access device of claim 1, wherein the distal opening of the vent lumen is axially spaced from the distal opening of the fluid lumen, the vent lumen positioned closer to the distal end of the spike member than the fluid lumen.

7. The vial access device of claim 1, wherein the distal end of the spike member is pointed and configured to pierce a stopper.

8. The vial access device of claim 7, wherein the distal opening of the fluid lumen extends in a longitudinal direction of the spike member.

9. The vial access device of claim 1, further comprising a lubricant coating positioned on the spike member.

10. The vial access device of claim 9, wherein the lubricant coating is positioned adjacent to the distal end of the spike member.

11. The vial access device of claim 1, further comprising a pressure equalization chamber in fluid communication with the vent lumen.

12. The vial access device of claim 1, further comprising a pierceable membrane positioned adjacent to the first connector, the pierceable membrane covering a proximal opening of the fluid lumen.

13. The vial access device of claim 1, wherein the first connector comprises a neck portion of the housing defining an opening that is configured to receive a corresponding connector of a syringe adapter.

14. The vial access device of claim 1, wherein the second connector comprises a plurality of hook elements configured to engage a medical vial and secure the vial access device to the medical vial.

15. The vial access device of claim 1, wherein a cross-section transverse to a longitudinal axis of the spike member includes a y-axis and an x-axis, wherein a dimension of the spike member along the x-axis adjacent to the fluid lumen is larger than a dimension of the spike member along the x-axis adjacent to the vent lumen.

16. A vial access device comprising:
   a housing having first and second connectors, the first connector configured to be secured to a first container, the second connector configured to be secured to a second container;
   a spike member extending from the housing and having a proximal end and a distal end, the spike member defining a vent lumen and a fluid lumen spaced from the vent lumen, each of the vent lumen and the fluid lumen having a distal opening, wherein the distal openings of the vent lumen and the fluid lumen are each defined by a top edge and a bottom edge spaced axially from the top edge, wherein the spike member comprises a ring spaced and extending radially outward from the circumference of the spike member, and wherein the ring is configured to rest within a seal of the second container upon insertion of the spike member into the second container.

17. The vial access device of claim 16, wherein an outer portion of the top edges of the vent lumen and the fluid lumen are smooth and configured to substantially prevent coring of a stopper when penetrating the stopper with the spike member, and wherein the top edges of the vent lumen and the fluid lumen are chamfered.

18. The vial access device of claim 16, wherein the distal opening of the vent lumen is axially spaced from the distal opening of the fluid lumen, the vent lumen positioned closer to the distal end of the spike member than the fluid lumen.

19. The vial access device of claim 18, wherein the distal end of the spike member is pointed and configured to pierce a stopper, and wherein the distal opening of the fluid lumen extends in a longitudinal direction of the spike member.

20. A drug transfer system comprising:
a syringe adapter configured to be secured to a first container;
a vial access device comprising:
a housing having first and second connectors, the first connector configured to be secured to the syringe adapter, the second connector configured to be secured to a second container;
a spike member extending from the housing and having a proximal end and a distal end, the spike member defining a vent lumen and a fluid lumen spaced from the vent lumen, each of the vent lumen and the fluid lumen having a distal opening, wherein a shape defined by a circumference of the spike member is only symmetric about one axis at a position between the proximal end of the spike member and the distal opening of the fluid lumen, wherein the circumference of the spike member varies in size and shape between the proximal end of the spike member and the distal opening of the fluid lumen.

21. The drug transfer system of claim 20, wherein the spike member comprises a ring extending radially outward from the spike member, wherein the ring is configured to engage a portion of a stopper upon penetrating the stopper with the spike member, and wherein a circumference of a portion of the spike member that is positioned distally of the ring is larger than a circumference of a portion of the spike member that is positioned adjacent to the distal openings of the vent and fluid lumens.

* * * * *